United States Patent
Celli et al.

[11] 3,951,876
[45] Apr. 20, 1976

[54] ODORIFEROUS COMPOSITIONS CONTAINING CERTAIN CYCLOPENTANONE DERIVATIVES

[75] Inventors: Charles Jerome Louis Celli, Eaubonne; Marcel Plattier, Antibes; Paul José Teisseire, Grasse, all of France

[73] Assignee: Societe Anonyme des Etablissements Roure-Bertrand Fils & Justin Dupont, Paris, France

[22] Filed: Jan. 11, 1973

[21] Appl. No.: 322,747

[30] Foreign Application Priority Data
Jan. 18, 1972  France .................. 72.01509

[52] U.S. Cl. .................. 252/522; 424/76; 424/364
[51] Int. Cl.[2] .......................... C11B 9/00
[58] Field of Search .................... 252/522

[56] References Cited
UNITED STATES PATENTS
3,845,133  10/1974  Cohen et al. .................. 252/522

*Primary Examiner*—Donald B. Moyer
*Attorney, Agent, or Firm*—Wallenstein, Spangenberg, Hattis & Strampel

[57] ABSTRACT

Novel odoriferous compositions which contain as an odoriferous material certain cyclopentanone derivatives having the formula

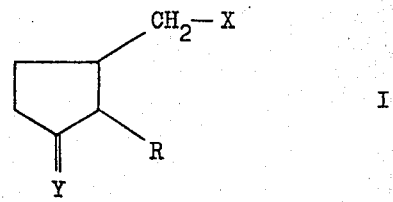

I in which
  R represents a hydrocarbon group of 3 to 7 carbon atoms,
  X represents a cyano, formyl, hydroxymethyl, lower alkoxymethyl, lower alkanoyloxymethyl or lower alkylcarbonyl group and
  Y represents an oxo or ketal group,
with the proviso that R does not represent an n-pentyl group when, simultaneously, X represents a methylcarbonyl group and Y represents an oxo group.

19 Claims, No Drawings

ODORIFEROUS COMPOSITIONS CONTAINING CERTAIN CYCLOPENTANONE DERIVATIVES

DETAILED DESCRIPTION OF THE INVENTION

The present invention relates to novel odoriferous compositions which contain as an odoriferous material certain cyclopentanone derivatives.

The cyclopentanone derivatives utilized as odoriferous materials according to the invention have the formula

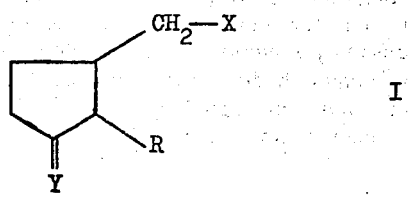

I wherein
  R represents a hydrocarbon group having from 3 to 7 carbon atoms,
  X represents a cyano, formyl, hydroxymethyl, lower alkoxymethyl, lower alkanoyloxymethyl or lower alkylcarbonyl group and
  Y represents an oxo or ketal group, with the proviso that R does not represent an n-pentyl group when, simultaneously,
  X represents an acetyl group and Y represents an oxo group.

R may represent a saturated or unsaturated, aliphatic, aromatic or araliphatic hydrocarbon group, which may be a straight chain group, a branched chain or a cyclic group. R may thus, for example, represent an alkyl, alkenyl, aryl, aralkyl, cycloalkyl or cycloalkylalkyl group. Specific examples of such groups include n-propyl, isopropyl, n-butyl, sec. butyl, tert. butyl, n-pentyl, isopentyl or a hexyl or heptyl group, or a corresponding ethylenically unsaturated group, cyclopentyl, cyclopentylmethyl, cyclopentylethyl, cyclohexylmethyl, cyclopropylethyl, phenyl or benzyl.

Where R contains a cyclic moiety it is preferred that the cyclic moiety be linked to the cyclopentanone nucleus via a methyl or ethyl linkage.

Especially preferred compounds, according to this invention, are those in which R represents an n-pentyl group inasmuch as these compounds have particularly remarkable odoriferous properties.

The lower alkyl and lower alkoxy groups as well as the alkyl moiety of the lower alkanoyl groups in the substituent X are defined as being such groups containing from 1 to 6 carbon atoms in the alkyl moiety. Examples of such alkyl moieties include methyl, ethyl, propyl, isopropyl, n-butyl, isobutyl, n-pentyl and n-hexyl.

The ketal group may be a cyclic ketal group containing 2 or 3 carbon atoms or a di-lower alkoxy group in which the lower alkoxy groups each contain up to 4 carbon atoms. The compounds in which Y represents a ketal group may thus be represented by the formula:

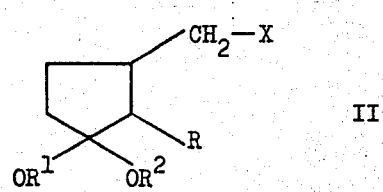

II in which R and X have the meanings given above and $R^1$ and $R^2$ each represent a lower alkyl group containing up to 4 carbon atoms, or $R^1$ and $R^2$ taken together represent a lower alkylene group having 2 or 3 carbon atoms. $R^1$ and $R^2$ preferably represent methyl or ethyl groups or, when taken together, an ethylene group.

Examples of odoriferous compounds according to the present invention include: 3-cyanomethyl-2-n-pentyl-1-cyclopentanone; 3-cyanomethyl-2-isopropyl-1-cyclopentanone; 3-cyanomethyl-2-(2-n-hexenyl)-1-cyclopentanone; 3-cyanomethyl-1,1-ethylenedioxy-2-n-pentyl-cyclopentane; 3-cyanomethyl-2-cyclopentylmethyl-1,1-ethylenedioxy-cyclopentane; 3-formylmethyl-2-n-butyl-1-cyclopentanone; 3-formylmethyl-2-n-pentyl-1-cyclopentanone; 3-formylmethyl-2-benzyl-1-cyclopentanone; 2-cyclopentylmethyl-3-formylmethyl-1-cyclopentanone; 1,1-ethylenedioxy-3-formylmethyl-2-isopropyl-cyclopentane; 1,1-ethylenedioxy-3-formylmethyl-2-n-pentyl-cyclopentane; 3-hydroxyethyl-2-n-pentyl-1-cyclopentanone; 3-hydroxyethyl-2-(2-n-pentenyl)-1-cyclopentanone; 2-cyclopropylethyl-3-hydroxyethyl-1-cyclopentanone; 1,1-ethylenedioxy-3-hydroxyethyl-2-n-pentyl-cyclopentane; 2-cyclohexylmethyl-1,1-ethylenedioxy-3-hydroxyethylcyclopentane; 2-(cyclopropyl-n-propyl)-1,1-ethylenedioxy-3-hydroxymethylcyclopentane; 2-cyclohexylmethyl-3-methoxyethyl-1-cyclopentanone; 2-n-pentyl-3-n-propoxymethyl-1-cyclopentanone; 2-(2-n-butenyl)-3-n-hexyloxymethyl-1-cyclopentanone; 1,1-ethylenedioxy-2-n-pentyl-3-n-pentyloxymethyl-cyclopentane; 1,1-ethylenedioxy-2-n-pentyl-3-n-propionyloxymethyl-cyclopentane; 1,1-ethylenedioxy-3-isopentanoyloxymethyl-2-isopentylcyclopentane; 3-acetoxyethyl-1,1-ethylenedioxy-2-n-pentyl-cyclopentane; 3-acetoxymethyl-1,1-ethylenedioxy-2-n-hexyl-cyclopentane; 3-acetoxyethyl-2-n-pentyl-1-cyclopentanone; 2-n-pentyl-3-n-propionyloxymethyl-1-cyclopentanone; 2-n-pentyl-3-propionylmethyl-1-cyclopentanone; 3-acetylmethyl-2-n-butyl-1-cyclopentanone; 3-acetylmethyl-2-(2-n-hexenyl)-1-cyclopentanone; 3-n-hexanoylmethyl-2-n-pentyl-1-cyclopentanone; 3-acetylmethyl-1,1-ethylenedioxy-2-n-pentyl-cyclopentane; 1,1ethylenedioxy-3-isobutyrylmethyl-2-n-pentyl-cyclopentane.

Certain of the odoriferous compounds, utilized in odoriferous compositions of the present invention, which have the formula:

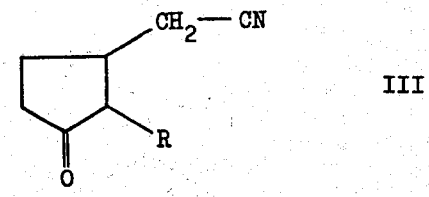

III wherein R has the meaning given above, may be prepared by hydrolysing and decarboxylating a compound having the formula:

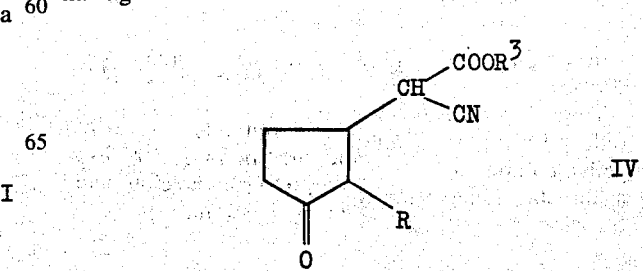

IV in which R has the meanings given above and $R^3$ represents a lower alkyl group having from 1 to 4 carbon atoms, preferably methyl or ethyl.

The odoriferous compounds of formula I in which R, X and Y have the meanings given above, as qualified by the proviso, with the exception of those compounds in which X represents a lower alkylcarbonyl group, may all be prepared by the processes using the 3-cyanomethyl compound of formula III as starting material. The compounds of formula I may be prepared by a process which involves firstly ketalising the compound of formula III in order to obtain the corresponding ketal having the formula

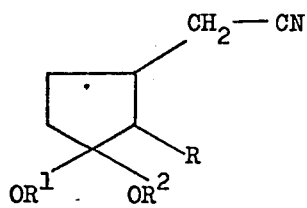

V in which R, $R^1$ and $R^2$ have the meanings given above, followed by reduction of the cyano group and if desired, elimination of the ketal group in order to regenerate the 1-keto group.

The ketals of formula V may be prepared by treating the corresponding ketone with a lower alkylene glycol such as ethylene glycol or propylene glycol or with a mixed orthoformate of a lower alkyl ethylene glycol in the presence of an acid catalyst. The di-lower alkoxy ketals may be prepared by reacting the corresponding ketone with a lower alkyl orthoformate in the presence of an acid catalyst.

The reaction conditions and the reactants utilised to effect the reduction of the cyano group depend on the compound to be prepared. For the preparation of compounds in which X represents a formyl group, the reduction can be effected with the aid of diisobutyl aluminium hydride, to obtain compounds having the formula:

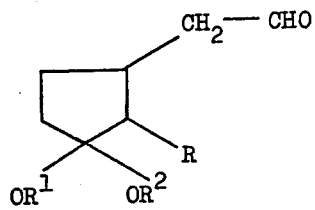

VI in which R, $R^1$ and $R^2$ have the meanings given above.

The compounds of formula VI can either be further reduced in order to obtain a corresponding 3-hydroxyethyl compound or the ketal group may be eliminated at this stage, in order to obtain a compound having the formula:

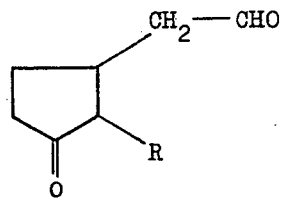

VII in which R has the meanings given above.

The reduction of the 3-formylmethyl compounds of formula VI to give the corresponding 3-hydroxyethyl compounds corresponding to formula VIII may be effected, for example by the use of a complex of diisobutylaluminium hydride with pyridine, lithium aluminium hydride orisopropyl alcohol in the presence of aluminium isopropylate.

The resulting compounds having the formula:

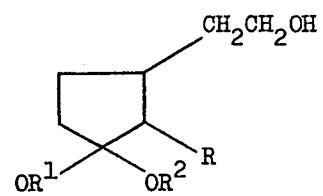

VIII in which R, $R^1$ and $R^2$ have the meanings given above, may then be either esterified or etherified to give the corresponding compounds of formula I in which X represents a lower alkoxymethyl or lower alkanoyloxymethyl group and R has the meanings given above, or the ketal group may be eliminated to give compounds having the formula:

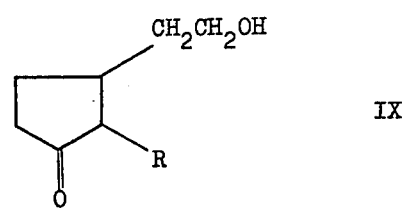

IX in which R has the meanings given above.

The etherification or esterification reactions gives compounds of formula:

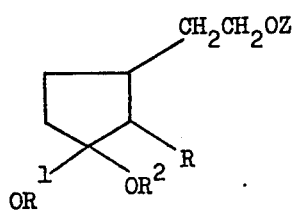

X wherein

Z represents a lower alkyl or lower alkylcarbonyl group in which the alkyl groups and moieties contain from 1 to 6 carbon atoms, and R, R¹ and R² have the meanings given above.

If desired, the ketal group can be eliminated from the compounds of formula X to give the corresponding 1-oxo compounds of formula:

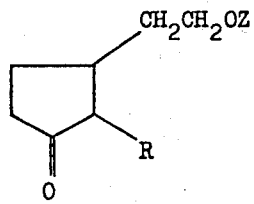

XI in which R and Z have the meanings given above.

In all of the processess involving the replacement of the ketal group by the 1-oxo group, the reaction may be effected, for example, by heating in the presence of excess acetone, and preferably, in the presence of an acid catalyst such as p-toluenesulphonic acid.

Those of the odoriferous compounds utilized according to the present invention having the formula:

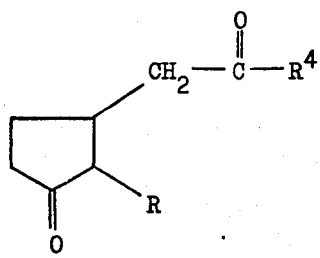

XII wherein

R⁴ represents a lower alkyl group having from 1 to 6 carbon atoms and R has the meaning given above. with the proviso that R does not represent an n-pentyl group when R⁴ represents methyl, may conveniently be prepared by hydrolysis and decarboxylation of a compound of formula:

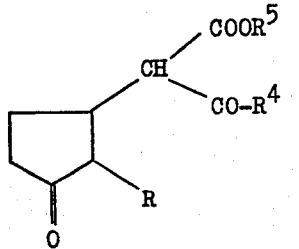

XIII wherein R and R⁴ having the meanings given in the proceding paragraph and R⁵ represents a lower alkyl group having from 1 to 4 carbon atoms, preferably methyl or ethyl.

The hydrolysis and decarboxylation may be effected by any convenient method. One convenient process comprises effecting the reaction with water, under pressure and in a medium which is initially substantially neutral. This reaction is conveniently effected at a temperature of from 120° to 300°C and, preferably, from 140° to 250°C. It is preferred to effect the reaction using the same weight of water and starting material. Under normal conditions, the reaction is effected in an autoclave which has been previously purged of air.

The starting material of formula IV may be prepared in convenient manner by condensing cyclopent-2-en-1-one having a hydrocarbon group in position 2 with a lower alkyl cyanoacetate.

The starting material of formula XIII may conveniently be prepared from a cyclopent-2-en-1-one having a hydrocarbon group in position 2, by condensation thereof with an alkyl acyl acetate having the formula:

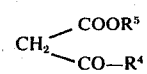

XV in which R⁴ and R⁵ have the meanings given above.

The intermediates of the aforementioned formula IV are useful for the preparation of 3-cyanomethyl compounds of formula III as defined above.

Further intermediates having the formula XIII are useful for the preparation of compounds of formula XII as defined above.

The odoriferous derivatives have valuable odorant properties. In general, the predominant odorant note of the compounds is a floral note. The odours of the free ketones are generally more pronounced than those of the ketals from which they are derived. Considered individually, certain compounds according to the invention present a variety of other interesting notes, for example green, fruity notes as well as the odour of newly woven fabric. Thus, for example, 3-acetoxyethyl-2-n-pentyl-cyclopentanone possesses floral and fruity notes, 3-formylethyl-2-n-pentyl-cyclopentanone possesses floral and green notes and an odour reminiscent of lilies, 3-hydroxyethyl-2-n-pentyl-cyclopentanone has a very delicate floral odour reminiscent of lily of the valley and of cyclamen, 3-cyanomethyl-2-n-pentyl-cyclopentanone has a floral odour of the jasmin type, 1,1-ethylenedioxy-3-formyl-2-n-pentyl-cyclopentane has an odour of bitter oranges, and 3-cyanomethyl-1,1-ethylenedioxy-2-n-pentyl-cyclopentane has a floral odour.

The odoriferous compounds according to the invention may be used in perfume concentrates and perfumed products in any desired combination, depending on the intensity of the floral and other notes required. In perfumes, they may conveniently be used in a proportion of up to 20%, for example 0.5 to 20%, by weight. The compounds can be used alone, or more preferably with other odorant substances, diluents and conventional fixatives for perfuming eau de cologne, toilet waters, cosmetics washing agents, aerosol and soap compositions, etc...

The invention will now be illustrated with reference to the following Examples.

Example 1

Into a 6 liter reactor provided with a stirrer, a dropping funnel and a vent are introduced 760 g of 2-n-pentylcyclopent-2-en-1-one, 1130 g of ethyl cyanoacetate and 625 g of absolute tertiary amyl alcohol. After one hour, 560 ml of a 1.78 N toluene solution of sodium tert. amylate are introduced whilst maintaining the temperature between 19 and 29°C. The mixture is then left for 16 hours at ambient temperature. The mass is then cooled to −5°C and neutralised with 5% aqueous sulphuric acidic solution. The reaction product is decanted and extracted with toluene; the toluene solutions are washed to neutrality and distilled. There is thus obtained 1850 g of crude product which is rectified under reduced pressure to give 1116 g of pure 3-carbethoxycyanomethyl-2-n-pentyl-1-cyclopentanone. This represents a yield of 84.2% (without taking into account the 2-n-pentyl-cyclopent-2-en-1-one recovered). The product shows the following constants: $b.p_{0.3} = 155 - 157°C$, $n_D^{15} = 1.4686$. The principal bands of its infra-red spectrum are as follows:

| | |
|---|---|
| 2250 cm$^{-1}$ | $v$ (C≡N): saturated nitrile |
| 1740 cm$^{-1}$ (broad) | $v$ (C=O): saturated ester + cyclopentanone |
| 1405 cm$^{-1}$ | $\delta$ (CH$_2$): $\alpha$ to the carbonyl group |
| 1250 and 1190 cm$^{-1}$ | $v$ (C—O): in the ester group |
| 720 cm$^{-1}$ | $\rho$ (CH$_2$)$_n$: in the n-pentyl group |

Examination of the N.M.R. spectrum of the product indicates the presence of a mixture due to 3 centres of asymmetry. The CH$_2$ of the ethyl group is exhibited in the form of 3 quadruplets and the H $\alpha$ to the CO in the form of 2 doublets.

Example 2

Into a 10 liter autoclave are introduced 1113 g of 3-carbethoxycyanomethyl-2-n-pentyl-1-cyclopentanone, 2184 ml of water, 67.2 ml of pyridine and 4.2 g of copper powder. The autoclave is closed, a vacuum created therein (20 mm) and then heated with mechanical stirring for 2½ hours. After 1½ hours, the temperature of the mass is 195°C and the interior pressure of the autoclave is 22 kg/cm$^2$. After cooling, extraction, washing and distillation of solvent, there are obtained 734 g of crude product which on rectification yields: 320 g of 2-n-pentyl-cyclopent-2-en-1-one, followed by 323 g of 3-cyanomethyl-2-n-pentyl-1-cyclopentanone.

The transformation rate of the reaction is consequently 68.8%. The product exhibits the following constants: $b.p_{0.4} = 122° - 125°C$, $n_D^{15} = 1.4700$.

| The infra-red spectrum principal bands at: | |
|---|---|
| 2240 cm$^{-1}$ | $v$ (C≡N): saturated nitrile |
| 1740 cm$^{-1}$ | $v$ (C=O): cyclopentanone |
| 1405 cm$^{-1}$ | $\delta$ (CH$_2$): $\alpha$ to the carbonyl group |
| 1420 cm$^{-1}$ | $\delta$ (CH$_2$): $\alpha$ to the nitrile group |
| 720 cm$^{-1}$ | $\rho$ (CH$_2$)$_n$: pentyl group |
| 1150 cm$^{-1}$ strong band. | |

With respect to the N.M.R. spectrum, apart from the triplet at $\delta = 0.88$ p.p.m. due to the methyl group on the end of the chain, the rest of the spectrum cannot be analysed because the presence of a mixture of two epimers.

Example 3

Into a 2 liter flask fitted with a 1 meter adiabatic column provided with a metallic lining, are placed: 400 g of 3-cyanomethyl-2-n-pentyl-1-cyclopentanone, 522 g of the glycoketal of methylethyl ketone and 4.5 g of paratoluenesulphonic acid. The mass is progressively heated in order to slowly distil the methyl ethyl ketone from the head of the column (temperature of the mass 128°–132°C; temperature of the vapour 80°C). The operation lasts about 5 hours. Then the excess glycoketal of methylethyl ketone is removed (temperature of the mass 132°–135°C; temperature of the vapour 110°–112°C). The mass is then cooled, 30 g of dry sodium carbonate added thereto, stirred for a half-hour and the mass washed to neutrality after diluting with 200 ml of ethyl ether. After distillation of the solvent and rectification of the crude product, there is obtained 360 g of 3-cyanomethyl-1,1-ethylenedioxy-2-n-pentyl-cyclopentane, which represents a yield of 73.4%. The product exhibits the following constants: $b.p_{0.5} = 136°–138°C$, $n_D^{15} = 1.4724$.

| The infra-red spectrum principal bands at: | |
|---|---|
| 2250 cm$^{-1}$ | $v$ (C≡N): saturated nitrile |
| 1420 cm$^{-1}$ | $\delta$ (CH$_2$): $\alpha$ to the nitrile group |
| 1150, 1115 and 1040 cm$^{-1}$ | $v$ (C—O): glycoketal. |

The N.M.R. shows a triplet at $\delta = 0.89$ p.p.m. due to CH$_3$ at the end of the chain and a double AB centre at 3.83 p.p.m. due to O—CH$_2$—CH$_2$—O. The rest of the spectrum indicates that a mixture of two epimers is present.

Example 4

Into a 5 liter flask fitted with a stirrer, dropping funnel and vent, are introduced 358.6 g of 3-cyanomethyl-1,1-ethylenedioxy-2-n-pentyl-cyclopentane dissolved in 755 ml of anhydrous petroleum ether. There is then added over one hour a solution of 280 g of diisobutylaluminium hydride in 755 ml of anhydrous petroleum ether, while maintaining the temperature between 25° and 30°C. After addition of the hydride, the temperature of the mass is held at 30°C for 2 hours and it is then diluted with 1,500 ml of technical petroleum ether. The whole of the solution is then added over 1 hour to 850 ml of a 10% aqueous solution of ammonium chloride while keeping the temperature in the region of 0°C. Into the so obtained mass, there is finally added, with constant stirring a solution of 396 g acetic acid in 3300 ml of water. The petroleum-ether solutions are decanted, washed to neutrality and distilled; they yield 345 g of crude product which is rectified under 1 mm Hg. There is thus obtained 250 g of 1,1-ethylenedioxy-3-formylmethyl-2-n-pentyl-cyclopentane, which represents a yield of 69%. The product exhibits the following constants: $b.p_{1.0.} = 120°–124°C$, $n_D^{15} = 1.4715$.

| The infra-red spectrum has principal bands at: | |
|---|---|
| 2710 cm$^{-1}$ | $v$ (C—H): saturated aldehyde |
| 1722 cm$^{-1}$ | $v$ (C=O): saturated aldehyde |
| 1150, 1118 and 1028 cm$^{-1}$ | $v$ (C—O): glycoketal |
| 720 cm$^{-1}$ | $\rho$ (CH$_2$)$_n$: pentane chain. |

The N.M.R. spectrum exhibits a triplet at $\delta = 0.86$ p.p.m. (CH$_3$ at the end of the chain), a spectral AB centre at 3.88 p.p.m. (4 H: dioxolane), a triplet (1 H) centre at 9.66 p.p.m. (—CH$_2$—CHO).

Example 5

A mixture of 24 g of 1,1-ethylenedioxy-3-formyl-methyl-2-n-pentyl-cyclopentane, 40 ml of dioxane, 32 ml of water and 0.18 g paratoluenesulphonic acid is refluxed for 3 hours. It is then cooled, 120 ml of water added and extracted three times with 100 ml of benzene. The benzene solutions are washed to neutrality and concentrated under reduced pressure. There are obtained 22 g of crude product which are rectified and which yield 15.5 g of product; b.p.$_{1.0}$ = 110°–140°C. The distillate is a mixture of keto aldehyde and the dioxolane of the aldehyde function (3-ethylenedioxymethyl-2-n-pentyl-1-cyclopentanone) in the proportions of 75/25. By careful rectification of this mixture, there is obtained 11 g of pure 3-formylmethyl-2-n-pentyl-1-cyclopentanone exhibiting: b.p.$_{0.5}$ = 90°C, N$_D^{15}$ = 1.4688.

| The infra-red spectrum has principal bands at: | |
|---|---|
| 2730 cm$^{-1}$ | $v$ (CH): aldehyde |
| 1725 cm$^{-1}$ | $v$ (C=O): saturated aldehyde |
| 1740 cm$^{-1}$ | $v$ (C=O): cyclopentanone |
| 1410 cm$^{-1}$ | $\delta$ (CH$_1$): $\alpha$ to the carbonyl |
| 720 cm$^{-1}$ | $\rho$ (CH$_2$)$_4$ |

The N.M.R. spectrum exhibits:
0.87 p.p.m. triplet due to CH$_3$ at the end of the chain
9.75 p.p.m. triplet due to the aldehyde proton (triplet complex arises from the fact that there is present a mixture of epimers).

Example 6

Into a one liter flask equipped as described in Example 1, are introduced: 42.6 g of diisobutylaluminium hydride dissolved in 100 ml of anhydrous benzene. Maintaining the temperature in the region of 0°C, 24 g pyridine is added thereto over 20 min. Still at the same temperature there is then added 60 g of 1,1-ethylenedioxy-3-formylmethyl-2-n-pentylcyclopentane dissolved in 125 ml of anhydrous benzene over 30 minutes. The reaction mass is then brought to 30°C and held at that temperature for 2 hours; it is then diluted with 250 ml benzene, cooled to 0°C and then poured into 135 ml of an iced 10% aqueous solution of ammonium chloride. A solution of 60 g acetic acid in 500 ml of water is then added. The benzene solutions are decanted, washed to neutrality and distilled. The crude product so obtained is rectified under 0.5 mm Hg. There is thus obtained 46 g of 1,1-ethylenedioxy-3-hydroxyethyl-2-n-pentyl-cyclopentane, which represents a yield of 76%. The product has the following constants: b.p.$_{0.5}$ = 122°–124°C, n$_D^{15}$ = 1.4775.

| The infra-red spectrum has principal bands at: | |
|---|---|
| 3400 cm$^{-1}$ | $v$ (OH): associated alcohol function |
| 1150 and 1115 cm$^{-1}$ | $v$ (C—O): glycoketal |
| 1035 cm$^{-1}$ | $v$ (C—O): primary alcohol (very strong band) |
| 720 cm$^{-1}$ | $\rho$ (CH$_2$)$_n$: pentane chain. |

Example 7

20.6 g of 1,1-ethylenedioxy-3-hydroxyethyl-2-n-pentylcyclopentane are mixed with 50 g of acetone and 0.162 g of paratoluenesulphonic acid. The mixture is brought to reflux during 1 hour, 0.26 ml of triethanolamine are then added thereto, the mixture concentrated on a water-bath under 25 mm Hg and the mass dissolved in 100 ml of benzene. The benzene solution, washed to neutrality and distilled under reduced pressure, yields 22 g of crude product which is rectified. There are thus obtained 15 g of 3-hydroxyethyl-2-n-pentylcyclopentanone which represents a yield of 89%.

The product has the following constants: b.p.$_{0.5}$ = 112°–115°C, n$_D^{15}$ = 1.4740.

| The infra-red spectrum has principal bands at: | |
|---|---|
| 3440 cm$^{-1}$ | $v$ (OH): associated alcohol functions |
| 1740 cm$^{-1}$ | $v$ (C=O): cyclopentanone |
| 1410 cm$^{-1}$ | $\delta$.(CH$_2$): $\alpha$ to the carbonyl group |
| 1050 cm$^{-1}$ | $v$ (C—O): primary alcohol function |
| 720 cm$^{-1}$ | $\delta$ (CH$_2$)$_n$: pentane chain. |

Example 8

1,1-Ethylenedioxy-3-hydroxyethyl-2-n-pentyl-cyclopentane (18.2 g) is mixed with 11.5 g acetic anhydride dissolved in 15 g of pyridine. The homogeneous mixture is left at ambient temperature for 15 hours and then brought during 1 hour to 95°C. 65 ml of water are then added and the mixture is stirred for 30 minutes at 95°C. After cooling, the mixture is extracted 3 times with 50 ml of benzene. The benzene solutions are washed to neutrality and concentrated under reduced pressure yielding 22 g of crude product which are rectified. There are thus obtained 19.9 g of 3-acetoxyethyl-1,1-ethylenedioxy-2-n-pentyl-cyclopentane (97.5% yield) exhibiting: b.p.$_{0.5}$ = 120°–125°C, n$_D^{15}$ = 1.4648.

| The infra-red spectrum has principal bands at: | |
|---|---|
| 1740 cm$^{-1}$ | $v$ (C=O): saturated ester |
| 1360 cm$^{-1}$ | $\delta$ (CH$_3$): in —CO—CH$_3$ |
| 1240 cm$^{-1}$ | $v$ (C—O): acetate |
| 1150, 1120 and 1040 cm$^{-1}$ | ethylene-ketal |
| 730 cm$^{-1}$ | $\rho$ (CH$_2$)$_n$ |

The N.M.R. spectrum exhibits:
0.88 p.p.m. triplet CH$_3$ at the end of the chain
1.95 p.p.m. singlet —CO—CH$_3$
3.80 p.p.m. triplet —CH$_2$—CH$_2$—OAc

Example 9

A mixture of 7.1 g of 2-acetoxyethyl-1,1-ethylenedioxy-2-n-pentyl-cyclopentane, 14.5 g of acetone and 0.0475 g of paratoluenesulphonic acid is brought to reflux during 1 hour. There is added thereto 0.08 mole of triethanolamine and the mixture is concentrated under reduced pressure on a water-bath. The residue is dissolved in 50 ml of benzene and washed with water until neutral. The distilled benzene solution yields 7 g of crude product which are rectified. There are obtained 5 g of 3-acetoxyethyl-2-n-pentyl-1-cyclopentanone (83.3% yield) having b.p.$_{0.5}$ = 110°–113°C, n$_D^{15}$ = 1.4610.

| The infra-red spectrum has principle bands at: | |
|---|---|
| 1740 cm$^{-1}$ | $v$ (C=O): saturated ester plus cyclopentanone |
| 1410 cm$^{-1}$ | $\delta$ (CH$_2$): $\alpha$ to a carbonyl |
| 1240 cm$^{-1}$ | $v$ (C—O): acetate |
| 725 cm$^{-1}$ | $\rho$ (CH$_2$)$_n$ |

The N.M.R. spectrum exhibits:
0.88 p.p.m. triplet CH$_3$ at the end of the chain
1.98 p.p.m. singlet —CO—CH$_3$
4.10 p.p.m. triplet —CH$_2$CH$_2$—OAc

Example 10

Into a 2 liter glass flask equipped as in Example No. 1, are added 152 g of 2-n-pentyl-cyclopent-2-en-1-one and 216 g of ethyl propionylacetate. Then, maintaining the temperature at 20°C, there are added over 1 hour 250 g of a 22% solution of sodium tert. amylate in toluene and then 125 g of anhydrous tertiary amyl alcohol. The temperature is then brought to 35°C and maintained for 24 hours, then the mixture is neutralised with 500 g of a 5% aqueous solution of sulphuric acid. The aqueous phase is extracted twice with 50 ml of toluene. The toluene solutions are combined, washed to neutrality and distilled. By rectification of the residue there are obtained: 90 g of pentylcyclopentanone, 132 g of ethyl propionylacetate and a residue of 120 g. The latter, subjected to a molecular distillation (1/100 mm Hg) yields 112 g of diketoester [2-n-pentyl-3-(1-carbethoxy-2-oxo-n-butyl)- 1-cyclopentanone], which represents a yield of 92% in relation to pentylcyclopentenone actually used.

The product had the following physical constants: $n_D^{20} = 1.4658$ $d20/4 = 1.0275$.

Example 11

Into a one liter autoclave, there are introduced: 187 g of 2-n-pentyl-3-(1-carbethoxy-propionylmethyl-1-cyclopentanone and 187 g of distilled water. The autoclave is evacuated and rapidly heated to 140°C, which temperature is maintained for 3 hours. After cooling and decompression, the mass is extracted with benzene. The benzene solutions are washed with water and distilled; theere are thus obtained 3 g of pentylcyclopentanone and 132 g of 2-n-pentyl-3-propionyl-methyl-1-cyclopentanone, which represent a yield of 82.5% in relation to the diketoester actually used up. The product has the following physical constants: b.p.$_1$ = 126°C; $n_D^{20} = 1.4692$; $d20/4 = 0.9525$ The following examples A to E hereafter illustrate odoriferous compositions according to the present invention.

| Example A Parts by weight | Perfume with Hyacinth odour |
|---|---|
| 168 | Bergamot peel oil extra |
| 90 | Lemon oil ordinary |
| 36 | Linalol |
| 27 | Argeol |
| 18 | Cinnamic alcohol synthetic |
| 126 | Phenylethyl alcohol |
| 36 | Phenylethyl acetate |
| 72 | Hydroxycitronellal |
| 18 | Terpineol |
| 18 | Eugenol extra |
| 3.5 | Galbanum oil |
| 9 | Styrallyl acetate |
| 63 | Phenylacetaldehyde 50% |
| 18 | Styrax oil |
| 90 | Benzyl salicylate |
| 54 | Hibiscolide |
| 36 | Jasmin absolute |
| 18 | Vetiver Bourbon oil |
| 9 | Vanillin |
| 27 | Tonka bean absolute |
| 3.5 | Tuberose absolute |
| 60 | 3-Formylmethyl-2-n-pentyl-cyclopentanone |
| 1000 | |

| Example B Parts by weight | Rose perfume |
|---|---|
| 86 | Linalyl acetate |
| 143 | Terpenyl acetate |
| 86 | Phenylethyl alcohol |
| 28 | Citronellol |
| 14 | Cinnamic alcohol |
| 28 | Linalol |
| 7 | Geraniol |
| 115 | Terpineol |
| 215 | Hydroxycitronellal |
| 71 | Styrax oil |
| 21 | Methylionone |
| 21 | Eugenol |
| 14 | Phenylacetaldehyde |
| 14 | Hexylcinnamicaldehyde |
| 21 | Phenylacetaldehyde-dimethyl-acetal |
| 14 | Sandalwood oil |
| 28 | Jasmin absolute |
| 4 | Oriental Rose oil |
| 70 | 3-Formylmethyl-2-n-pentyl-cyclopentanone |
| 1000 | |

| Example C Parts by weight | Perfume concentrate |
|---|---|
| 40 | Phenylethyl alcohol |
| 100 | Bergamot peel oil extra |
| 40 | Lemon peel oil extra |
| 50 | Lavender oil Laragne 50% |
| 10 | Trimethyl undecanal, 10% in ethyl phthalate |
| 40 | Ylang Ylang oil Nbe extra |
| 20 | Rose of May absolute |
| 10 | C. 11 aldehyde 100%, 10% in ethyl phthalate |
| 20 | C. 12 aldehyde L 50%, 10% in ethyl phthalate |
| 30 | Essence galbanum, 10% in ethyl phthalate |
| 60 | Geraniol |
| 150 | Hydroxycitronellal |
| 40 | Jasmin absolute |
| 30 | Guaiol acetate |
| 10 | Forest moss absolute |
| 30 | Patchouly oil |
| 30 | Coumarin |
| 40 | Mixture of 1-ethoxy-4-(1-ethoxy-vinyl)-3,3,5,5-tetramethylcyclo-1-hexene and 4-(1-ethoxyvinyl)-3,3,5,5-tetramethyl-cyclohexanone |
| 20 | hibiscolide |
| 30 | Musk ketone |
| 200 | 3-hydroxymethyl-2-n-pentyl-cyclopentanone |
| 1000 | |

| Example D Parts by weight | Space deodorant |
|---|---|
| 75 | Benzyl acetate |
| 25 | Linalyl acetate |
| 65 | Hydroxycitronellal |
| 200 | Phenyl ethyl alcohol |
| 50 | Linalol |
| 100 | Terpineol |
| 100 | Geraniol |
| 25 | Ylang-Ylang third |
| 5 | Methyl anthranylate |
| 5 | Indolene, 1% in ethyl phthalate |
| 25 | Iso eugenol |
| 15 | Anisyl aldehyde |
| 50 | Styrallyl acetate, 10% |
| 25 | Santalol |
| 10 | Geranium Bourbon oil |
| 10 | Musk ambrette |
| 15 | Musk ketone |
| 200 | 3-Cyanomethyl-2-n-pentyl-cyclopentanone |
| 1000 | |

| Example E Parts by weight | Toilet water |
|---|---|
| 20 | Linalyl acetate |
| 50 | Lavender oil Laragne 50% |
| 70 | Linalol |
| 50 | Lemon peel oil extra |
| 50 | Mandarin oil extra |
| 20 | Menthol |
| 10 | Ylang-Ylang Nossi-Be extra |
| 100 | Hydroxycitronellal |
| 20 | Clary sage oil |
| 60 | Vetiveryl acetate |
| 30 | Caryophyllenyl acetate |
| 30 | East Indien Sandalwood oil |
| 60 | Methylionone |
| 60 | Amyl salicylate |
| 80 | Benzyl salicylate |
| 20 | Patchouly oil, Grasse |
| 30 | Coumarin |
| 70 | Resinoid benzoin |
| 20 | Musk ketone |
| 150 | 1,1-Ethylenedioxy-3-formyl-methyl-2-n-pentyl-cyclopentane |
| 1000 | |

What is claimed:

1. An odoriferous composition comprising a cyclopentanone derivative of the formula

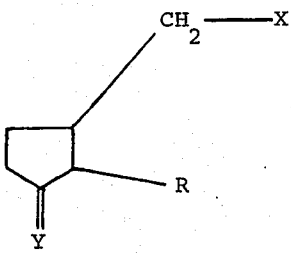

in which
R represents a hydrocarbon group of 3 to 7 carbon atoms,
X represents a cyano, formyl, hydroxymethyl, lower alkoxymethyl, lower alkanoyloxymethyl or lower alkylcarbonyl group and
Y represents an oxo or ketal group,
with the proviso that R does not represent an n-pentyl group when, simultaneously, X represents a methylcarbonyl group and Y represents an oxo group, in admixture with a carrier which is perfumed by said cyclopentanone derivative.

2. An odoriferous composition according to claim 1, wherein Y represents an oxo group.

3. An odoriferous composition according to claim 1, wherein Y represents a cyclic ketal group of 2 or 3 carbon atoms.

4. An odoriferous composition according to claim 3, wherein Y represents an ethylenedioxy group.

5. An odoriferous composition according to claim 1, wherein Y represents the group

in which
$R^1$ and $R^2$ represent lower alkyl groups of up to 4 carbon atoms.

6. An odoriferous composition according to claim 5, wherein $R^1$ and $R^2$ each represent a methyl or ethyl group.

7. An odoriferous composition according to claim 1, wherein R represents an alkyl group of 3 to 7 carbon atoms.

8. An odoriferous composition according to claim 1, wherein R represents an n-pentyl group.

9. An odoriferous composition according to claim 1, in which said cyclopentanone derivative is 3-cyanomethyl-2-n-Pentyl-1-cyclopentanone.

10. An odoriferous composition according to claim 1, in which said cyclopentanone derivative is 3-cyanomethyl-1,1-ethylenedioxy-2-n-pentyl-cyclopentane.

11. An odiriferous composition according to claim 1, in which said cyclopentanone derivative is 1,1-ethylenedioxy-3-formylmethyl-2-n-pentyl-cyclopentane.

12. An odoriferous composition according to claim 1, in which said cyclopentanone derivative is 3-formylmethyl-2-n-pentyl-1-cyclopentanone.

13. An odoriferous composition according to claim 1, in which said cyclopentanone derivative is 1,1-ethylenedioxy-3-hydroxyethyl-2-n-pentyl-cyclopentane.

14. An odoriferous composition according to claim 1, in which said cyclopentanone derivative is 3-hydroxyethyl-2-n-pentyl-1-cyclopentanone.

15. An odoriferous composition according to claim 1, in which said cyclopentanone derivative is 3-acetoxyethyl-1,1-ethylenedioxy-2-n-pentyl-cyclopentane.

16. An odoriferous composition according to claim 1, in which said cyclopentanone derivative is 3-acetoxyethyl-2-n-pentyl-1-cyclopentanone.

17. An odoriferous composition according to claim 1, in which said cyclopentanone derivative is 2-n-pentyl-3-propionylmethyl-1-cyclopentanone.

18. An odoriferous composition according to claim 1, wherein R represents a 2-n-pentenyl group.

19. An odoriferous composition according to claim 1, which is in the form of a perfume.

* * * * *